(12) United States Patent
Naito

(10) Patent No.: US 6,936,589 B2
(45) Date of Patent: Aug. 30, 2005

(54) PARENTERAL DELIVERY SYSTEMS

(76) Inventor: Albert T. Naito, 2776 Cibola Ave., Costa Mesa, CA (US) 92626

( * ) Notice: Subject to any disclaimer, the term of this patent is extended or adjusted under 35 U.S.C. 154(b) by 478 days.

(21) Appl. No.: 09/967,791

(22) Filed: Sep. 28, 2001

(65) Prior Publication Data

US 2003/0064934 A1 Apr. 3, 2003

(51) Int. Cl.$^7$ .................. A61K 31/70; A01N 43/04
(52) U.S. Cl. ................. 514/25; 514/2; 514/23; 514/58; 514/62
(58) Field of Search ............... 514/2, 23, 25, 514/58, 62; 536/4.1, 18.7, 112, 55.2

(56) References Cited

U.S. PATENT DOCUMENTS

| | | | | |
|---|---|---|---|---|
| 4,025,650 | A | | 5/1977 | Gans et al. .................. 424/319 |
| 4,604,286 | A | | 8/1986 | Kawajiri ..................... 424/149 |
| 4,639,465 | A | | 1/1987 | Pollack et al. .............. 514/419 |
| 4,866,042 | A | * | 9/1989 | Neuwelt ....................... 514/44 |
| 5,059,415 | A | | 10/1991 | Neuwelt ......................... 424/9 |
| 5,686,416 | A | * | 11/1997 | Kozarich et al. ............. 514/15 |
| 5,972,924 | A | * | 10/1999 | Keep et al. ................. 514/183 |
| 6,294,520 | B1 | * | 9/2001 | Naito ........................... 514/23 |

FOREIGN PATENT DOCUMENTS

| | | | | |
|---|---|---|---|---|
| EP | 0 652 012 | A1 | * 5/1993 | ......... A61K/31/195 |
| EP | 0652012 | A1 | * 10/1995 | .......... A61K/31/70 |

OTHER PUBLICATIONS

Wurtman, RJ, Nutrients That Modify Brain Function, *Scientific American,* vol. 264(4):50–59(1982).

Goldstein, GW, and Betz, AL, The Blood–Brain Barrier, *Scientific American,* vol. 255(3):74–83 (Sep. 1986).

Johnson, LR (ed.), Physiology of the Gastrointestinal Tract, pp. 1478–1481 (1987).

* cited by examiner

*Primary Examiner*—James O. Wilson
*Assistant Examiner*—Patrick Lewis
(74) *Attorney, Agent, or Firm*—Howard Gisenberg, Esq.

(57) ABSTRACT

Hypertonic sugar compositions administered by other than ingestion and swallowing or intravascular injection, such as by intranasal spray or drops, intraocular drops or ointment, oral spray, intraotic spray or drops, lozenges, chewable tablet, chewing gum, or gargle, pulmonary inhalation, vaginal or rectal suppositories, or transdermal creams, ointments, lotions, or patches, are effective to open the blood-brain barrier to permit entry into the central nervous system of a co-administered chemical compound, such as a nutrient or a therapeutic or diagnostic agent. In this way, the compositions and methods of the invention increase the therapeutic or diagnostic efficacy of such chemical compounds.

27 Claims, No Drawings

PARENTERAL DELIVERY SYSTEMS

FIELD OF THE INVENTION

The present invention relates to the field of delivering therapeutic substances into the body. More particularly, the invention relates to delivering such substances into the brain by temporarily opening the blood-brain barrier.

BACKGROUND OF THE INVENTION

The blood-brain barrier that exists in all vertebrate brains was discovered in the latter part of the $19^{th}$ century and the first half of the $20^{th}$ century. Researchers discovered that dyes injected intravenously into the bloodstream stained all internal organs except the brain and that dyes injected into the cerebrospinal fluid stained cells of the brain but did not enter the bloodstream to stain other internal organs. It was later discovered that the blood-brain barrier was due to the structure of the capillary walls of the brain.

In organs other than the brain, fluid leaks out of capillaries and enters the tissue through pores formed at the junction of adjacent endothelial cells. In the brain, however, endothelial cells of capillaries are intimately fused by intercellular tight junctions. The tight junctions prevent the paracellular leakage of fluid from the capillaries, leaving transcellular flow from the capillary to the brain as the only means for fluid and solutes to enter the brain from the bloodstream.

Among the means of transcellular fluid flow available to other organs of the body, pinocytosis is virtually nonexistent in brain capillaries. Consequently, solutes may enter the brain in one of two ways. In facilitated transport, a specialized carrier or receptor catalyst molecule transports a particular molecule through the endothelial cell wall into the brain. In lipid-mediated transport, small lipid soluble molecules dissolve in and diffuse through the endothelial cell membrane.

While these mechanisms permit the entry into the brain of essential nutrients, the existence of the blood-brain barrier effectively prevents other substances, such as hormones, proteins, certain ions, and drugs, from entering the brain. Although it is normally quite useful to protect the brain from exposure to these substances, the blood-brain barrier also serves to prevent therapeutic or diagnostic agents from reaching the substance of the brain or the cerebrospinal fluid, rendering it difficult to treat or diagnose certain diseases.

Consequently, methods of penetrating the blood-brain barrier so as to permit entry of therapeutic or diagnostic substances have long been sought. Kozarich et al., U.S. Pat. No. 5,686,416, discloses that intravenous injection of certain peptide analogues of bradykinin increase the permeability of the blood-brain barrier to co-administered therapeutic or diagnostic agents. The peptides function by attaching to certain receptors on the surface of brain-blood barrier endothelial cells, which causes the blood-brain barrier to become permeable. As disclosed in Kozarich, only peptides having a particular amino acid sequence adopt the proper conformation to interact with the receptors and increase the permeability of the blood-brain barrier. Kozarich states that the peptides may be administered by several routes, including intravascular, subcutaneous, and intramuscular injection, and by oral, transdermal, intranasal, and inhalation administration. However, in all eleven examples of in vivo treatment with the peptides, only intravascular injections were shown to be effective.

In contrast to Kozarich, U.S. Pat. No. 4,866,042 (Neuwelt) and U.S. Pat. No. 5,059,415 (Neuwelt) disclose the opening of the blood-brain barrier by an osmotic disruption of the blood-brain barrier. According to Neuwelt, the blood-brain barrier is temporarily opened to permit the entry of genetic material and diagnostic imaging agents into the brain by the intraarterial injection of a hyperosmotic sugar, such as mannitol, arabinose, and glucose. The resultant hypertonicity of the blood adjacent to the cells of the blood-brain barrier causes these cells to shrink, leaving gaps between the cells. Compounds within the bloodstream can then enter the brain through these gaps. Neuwelt reports that, in contrast to the normal state in which the blood brain barrier excludes molecules having a molecular weight larger than 180 Daltons, when the blood-brain barrier is opened by osmotic disruption, molecules having a molecular weight of 1,000,000 Daltons can pass.

Naito, A., in European Patent No. 652012A1 and Canadian Patent No. 2,103,339, discloses that certain pure sugars in combination with certain amino acids, when administered orally or intravenously in sufficient quantities, have the ability to effect the entry of other materials across the blood-brain barrier. The disclosure of Naito represents an advance over that of Kozarich in that a peptide having a particular amino acid sequence is not necessary and a workable method of oral administration is disclosed. The disclosure of Naito represents an advance over that of Neuwelt in that intraarterial administration of the hyperosmotic agent is unnecessary in order to cause osmotic disruption of the blood-brain barrier. Rather, as discovered by Naito, the blood-brain barrier can be breached by less invasive methods of hypertonic sugar administration.

The method disclosed by Naito requires a substantial quantity of sugar and amino acid to be utilized. To deliver a therapeutic amount of most materials across the blood-brain barrier, however, an amount of sugar between 0.5 and 10 grams, preferably between 0.5 and 6 grams, and an amount of amino acids between 300 to 2000 mg is required. Consequently, only oral and injection routes of administration were disclosed by Naito as being effective.

The need remains, however, for methods to traverse the blood-brain barrier in patients, both human and animal, in which intravascular and oral administration is impractical, impossible, or otherwise undesirable.

U.S. Pat. No. 5,756,071 (Mattern) discloses that the intranasal administration of certain sex hormones and biogenic amines resulted in a higher concentration in the blood than if these substances were administered perorally. Neurologic symptoms were improved following intranasal administration compared with peroral administration, which improvement was attributed by the inventors to be due probably to easier passage through the blood-brain barrier following pernasal administration.

Mattern does not disclose the facilitated entry across the blood-brain barrier of any substance other than that which is itself administered pernasally.

SUMMARY OF THE INVENTION

The inventor has unexpectedly discovered that a hypertonic sugar composition is effective to promote the entry of a chemical substance, such as a nutrient or a diagnostic or therapeutic agent, across the blood-brain barrier when the composition is administered to an animal by other than by gastrointestinal absorption or intravascular injection. In particular, the invention provides for the promotion of the entry of a nutrient or a diagnostic or therapeutic agent across the blood-brain barrier by co-administering the agent with a hypertonic sugar composition, which sugar is administered by a route that permits absorption into the body through the nasal, ocular, oral, otic, rectal, vaginal, or upper respiratory mucosa, or through the skin or lungs.

In one embodiment, the invention is a method for promoting the entry of a chemical substance, which is typically a nutrient or a therapeutic or diagnostic agent, across the blood-brain barrier by co-administering the substance with a hypertonic composition containing one or more sugars, which composition is administered by a route that permits the absorption of the composition into the body across the nasal, ocular, oral, rectal, vaginal, or upper respiratory mucosa, or through the skin or lungs.

In another embodiment, the invention is a pharmaceutical composition which is a hypertonic sugar composition containing one or more sugars and a pharmaceutically acceptable carrier, which composition is in the form of an intranasal spray or drops, ear drops or spray, ophthalmic drops or ointment, throat spray, lozenge, chewing gum, chewable tablet, liquid gargle, skin patch, ointment, lotion, or cream, inhaler, or rectal or vaginal suppository.

In another embodiment, the invention is a pharmaceutical formulation which contains a hypertonic sugar composition of one or more sugars, a pharmaceutically acceptable carrier, and a therapeutic or diagnostic chemical compound, which formulation is in the form of an intranasal spray or drops, ophthalmic drops or ointment, throat or ear spray, lozenge, liquid gargle, chewable tablet, chewing gum, skin patch, ointment, lotion, or cream, inhaler, or rectal or vaginal suppository.

The methods and compositions of the invention are well suited for human and veterinary patients, especially those that have compromised gastrointestinal absorptive capacity or when intravascular, such as intravenous and intraarterial, administration is undesired. For example, the methods and compositions of the invention are well suited for patients suffering from AIDS, cancer, stroke, or diseases of the upper or lower alimentary tract, those patients undergoing radiation exposure of the throat or esophagus, comatose or sleeping patients, and others in which the ability to swallow or to pass food from the oropharynx to the stomach is impaired.

DETAILED DESCRIPTION OF THE INVENTION

The present invention increases the permeability of the blood-brain barrier to a molecule or chemical compound, which is typically a nutrient or a therapeutic or diagnostic agent. The level of the compound in the brain, following co-administration of a hypertonic sugar composition in accordance with the invention, is higher than when administered without the composition of the invention. Administration of the hypertonic sugar composition is by other than ingestion into the gastrointestinal tract or intravascular injection. Methods suitable for administration of the hypertonic sugar composition include intranasal, intraocular, intraotic, inhalation, transmucosal such as oral, buccal, or lingual mucosa, transdermal, and rectal or vaginal suppository.

The compositions according to the invention contain one or more suitable sugars in an amount effective to increase the permeability of the blood-brain barrier. Suitable sugars include (L) and (D) stereoisomers of monosaccharides, disaccharides, dextrans, sugar alcohols, and amino sugars. Examples of suitable sugars include, galactose, xylose, fructose, glucose, arabinose, ribose, lyxose, meso-erythritol, xylitol, dulcitol, myo-inositol, mannitol, sorbitol, adonitol, arabitol, cellobiose, maltose, raffinose, rhamnose, melibiose, fucose, maltodextrins, glucosamine, mannosamine, galactosamine, lactose, and sucrose. In this specification, the term "sugar" is defined to mean any of the suitable sugars listed in the preceding two sentences.

The sugar composition may optionally comprise one or more amino acids, such as disclosed in the above-mentioned Naito European and Canadian patent applications. Amino acids that are suitable for the composition and method of the invention include (L) and (D) stereoisomers of all naturally occurring amino acids. Examples of suitable amino acids include glutamine, lysine, arginine, alanine, isoleucine, asparagine, aspartic acid, cysteine, glutamic acid, glycine, histidine, leucine, methionine, phenylalanine, proline, serine, threonine, tryptophan, tyrosine, valine, taurine, ornithine, carnitine, and citrilline. Small peptides, defined herein as those having up to three amino acids, such as glutathione, are also suitable for the amino acids of the composition of the invention.

If desired, the amino acids may be administered by the ingestion of food sources, especially those that contain enzymes such as amylase, maltase, sucrase, tributyrinase, peptidase, peroxidase, trypsin, catalase, oxidase, polyphenol-oxidase, protease, phophatase, lactase, oleinase, glycogenase, invertase, urease, ereptase, peptase, saccharase, and tyrosinase. Such food sources include fruits, such as apple, banana, grape, mango, and strawberry, vegetables such as cabbage, corn, kidney bean, potato, sweet potato, and tomato, and other sources such as egg, meat, milk, soybean, rice, tapioca, maple sap, raw honey, sugar cane, and mushroom. Preferably, the amino acids, whether from a food source or from a processed amino acid source are administered in a form as described below.

The amounts and concentrations of sugar and the optional amino acid in the composition will vary depending upon the mode of administration and amount of the molecule that is to be transported across the blood-brain barrier. Generally, the concentration of sugar in the composition should be sufficient to provide for the absorption of about 125 mg or more of sugar into the bloodstream within a period of 30 minutes, preferably within 10 minutes, and most preferably within 1 to 2 minutes. The optional amino acid should be in a concentration to provide for the absorption into the bloodstream of at least 10 mg in the above time periods.

The term "co-administered", when used in this specification and in the claims, refers to administering the sugar composition and a chemical compound having a biologic effect, either by itself or in combination with other chemical compounds, at the same time or at different times, but close enough in time so that the sugar can augment the biologic effect of the compound, generally by increasing the passage of the compound from the bloodstream across the blood-brain barrier into the central nervous system. It is preferable that the chemical compound should be administered so that therapeutically or diagnostically effective levels are available within the bloodstream at a time when the level of sugar within the bloodstream is sufficient to temporarily open the blood-brain barrier to permit entry of a desired quantity of the chemical compound into the brain or other portions of the central nervous system.

Generally, sugar is rapidly removed from the bloodstream to enter the cells of the body. Consequently, if the sugar is administered before the therapeutic compound, it is preferred that the chemical compound be administered within about 30 minutes following sugar administration, preferably within 10 minutes following sugar administration, and most preferably within one to two minutes following sugar administration. In diabetics and other individuals in which sugar transport from the bloodstream is delayed, the administration of the chemical compound may be delayed if desired for up to several hours following sugar administration.

When the chemical compound is administered before the sugar, the time in which the sugar must be administered will vary depending on the particular chemical compound and how long it remains in the bloodstream. For compounds that are eliminated rapidly, it might be necessary to administer the sugar within 30 minutes, or even as rapidly as one to two minutes, after administration of the compound. On the other hand, for compounds that remain in the bloodstream for extended periods of time, the co-administration of the sugar may be several hours after administration of the compound.

The chemical compounds that are suitable for use with the method of the invention include, but are not limited to, amino acids, peptides, lipids including simple lipids like fats, fatty acids, and waxes, and conjugated lipids like lecithins, phospholipids, and cerebrosides, carbohydrates, enzymes, vitamins, minerals, herbs, ionic salts, and minerals. Examples of particular compounds that are suitable as the chemical compound of the invention include beta-carotene, xanthophyll, lecithin (phosphatidylcholine), tricalcium phosphate, fat soluble vitamins A, D, E, and K, water soluble vitamins B and C, tryptophan, melatonin, pyroxidine, selenium, choline, tyrosine, tryptophan, arginine, hydroxyproline, enzymes such as proteases, amylases, and lipases, potassium glutinate, calcium carbonate, sodium or potassium chloride, cysteine, and omega 3 and omega 6 fatty acids.

The chemical compound is administered in an amount sufficient to cause a biochemical effect in the body of the patient and may vary depending upon such variables as the particular compound administered, the condition that it is being administered to treat, the severity of the symptoms that the patient has, biologic effect or the intensity of biologic effect that is desired, and the amount of sugar that is co-administered with the therapeutic agent.

The route of administration of the chemical compound is immaterial to the method of the present invention. For example, the compound may be administered by intravenous, intraarticular, or subcutaneous injection, or by other enteral or parenteral routes, such as by ingestion, suppository, transdermal, transmucosal, inhalation, or intranasal routes.

The pharmaceutical compositions of the invention comprise one or more sugars in combination with a pharmaceutically acceptable carrier and optionally with an amino acid, which composition may be, for example, in such formulations as an intranasal spray or drops, ophthalmic drops or ointment, a throat or ear spray, a lozenge, a chewable tablet, chewing gum, a liquid gargle, a skin patch, ointment, lotion, or cream, a respiratory inhaler, or a rectal or vaginal suppository. The composition is used, in accordance with the method of the invention, to enhance the biological effect of a co-administered chemical compound, typically by causing an osmotic disruption of the blood-brain barrier which permits the chemical compound to enter the central nervous system where it exerts its biological effect. Chewable tablets and chewing gum are most preferred formulations because of the prolonged contact time of the composition of the invention and the oral mucosa during the chewing process.

One embodiment of the composition of the invention may be made by combining one or more sugars, and optionally one or more amino acids, with a pharmaceutically acceptable carrier in which the sugar, and the amino acid if present, is soluble. Another embodiment of the composition of the invention may be made by combining one or more sugars, and optionally one or more amino acids, a pharmaceutically acceptable carrier in which the sugar, and the amino acid if present, is soluble, and a chemical compound having a desired therapeutic or diagnostic effect. One skilled in the art of pharmaceutical formulation will be able to formulate the composition in the form of an intranasal or intraotic spray or drops, ophthalmic drops or ointment, a throat spray, a lozenge, a liquid gargle, a chewable tablet, chewing gum, a skin patch, skin cream, skin ointment, skin lotion, a respiratory inhaler, or a rectal or vaginal suppository.

The methods and compositions of the invention may be used for experimental, diagnostic, or therapeutic purposes. For example, they may be used to increase the uptake of beta-carotene from the bloodstream to the brain, for experimental or therapeutic purposes related to the effect of beta carotene on the treatment of skin diseases or on hair growth in balding men. Lecithin, choline, or phospholipids, either alone or with other chemical compounds, may be used in accordance with the method of the invention to investigate or treat central nervous injuries or diseases such as Alzheimer's Disease, stroke, Lou Gebrig's disease, and cerebral palsy. Ocular diseases or disorders related to vision may be investigated or treated with Vitamin E co-administered with a sugar as disclosed herein. Mental illness such as depression may be investigated or treated with chemical agents known to have an effect on these diseases, such as lithium, amino acids like tyrosine and tryptophan, or other psychotropic agents. Other examples diseases that can be treated or investigated in accordance with the method of the invention are disclosed in European Patent No. 652012A1, Canadian Patent No. 2,103,339, and U.S. Pat. No. 6,294,520.

Examples of Potential Uses of the Methods of the Invention Include:

1. For investigation or treatment of comatose individuals to deliver therapeutic or nutritional substances. Topical creams or lotions, or transdermal patches may be used, preferably on the skin of the neck, the back of the hand, or the arms. Intranasal, intraocular, and intraotic are also routes of delivery that may be used.

For investigation of disorders such as Alzheimer's Disease or certain cancers, especially in situations in which the patient has reduced ability or desire to eat. Topical creams, ointments, or lotions, or transdermal patches may be used, preferably on the skin of the neck, the back of the hand, or the arms. Intranasal, intraocular, and intraotic are also routes of delivery that may be used. For example, the sugar and amino acid composition may be combined in a paste or lotion to be rubbed into the skin. Such paste may contain tapioca as a source of amino acids and may be formulated to provide from 125 to 5000 mg of amino acid from a source like tapioca, such as 2000 mg, and from 125 to 5000 mg of sugar, such as 2000 mg. As another example, the sugar and amino acid composition may be formulated as an intranasal spray or drop, ophthalmic drop or ointment, or throat or ear spray to provide a patient with 125 to 5000 mg, preferably about 2000 mg, of amino acid and from 125 to 5000, preferably about 2000 mg, of sugar.

For investigation or treatment of certain infectious diseases, including diseases such as AIDS. Any of the above forms of therapy may be used. Another way to provide the sugar and optional amino acid in accordance with the invention is by a chewable table, for example one containing between 125 to 5000 mg of a maltodextrin, for example 750 mg, and 125 to 5000 mg of tapioca, for example 750 mg.

The compositions and formulations useful in the invention may be formulated by any means known in the art to make parenterally administered but non-injectable formulations. For example, methods for making oral, otic, ophthalmic, or nasal sprays, drops and ointments, liquid gargles, lozenges, skin patches, ointments, lotions, and creams, suppositories, chewable tablets, chewing gums, and inhalers are well known to those skilled in the art of formulating.

Further modifications, uses, and applications of the invention described herein will be apparent to those skilled in the art. It is intended that such modifications be encompassed in the following claims.

What is claimed is:

1. A method for increasing the effect of a chemical compound within the body of a patient comprising administering said chemical compound to said patient, co-administering with said chemical compound a hypertonic sugar composition by a route other than by enteral administration or intravascular injection, and permitting said sugar composition to increase said effect, wherein said increase in effect of said chemical compound by said hypertonic sugar composition is by increasing the passage of said compound through the patient's blood-brain barrier.

2. The method of claim 1 wherein said effect is a therapeutic effect.

3. The method of claim 1 wherein said hypertonic sugar composition is administered at the same time as said chemical compound.

4. The method of claim 1 wherein said hypertonic sugar composition is administered before the administration of said chemical compound.

5. The method of claim 1 wherein said hypertonic sugar composition is administered following the administration of said chemical compound.

6. The method of claim 1 wherein the sugar is a monosaccharide, disaccharide, dextran, sugar alcohol, or an amino sugar.

7. The method of claim 6 wherein the sugar is selected from the group consisting of galactose, xylose, fructose, glucose, arabinose, ribose, lyxose, meso-erythritol, xylitol, dulcitol, myo-inositol, mannitol, sorbitol, adonitol, arabitol, cellobiose, maltose, raffinose, rhamnose, melibiose, fucose, maltodextrins, glucosamine, mannosamine, galactosamine, lactose, and sucrose.

8. The method of claim 1 wherein said hypertonic composition comprises an amino acid or a small peptide.

9. The method of claim 8 wherein said amino acid is selected from the group consisting of glutamine, lysine, arginine, alanine, isoleucine, asparagine, aspartic acid, cysteine, glutamic acid, glycine, histidine, leucine, methionine, phenylalanine, proline, serine, threonine, tryptophan, tyrosine, valine, taurine, ornithine, carnitine, and citrulline.

10. The method of claim 1 wherein the route of administration of the sugar composition is selected from the group consisting of nasal, ocular, oral, rectal, vaginal, or upper respiratory mucosa, or through the skin or lungs.

11. A method for increasing the permeability of the blood-brain barrier comprising administering to a patient in need thereof a hypertonic sugar composition by a route other than by enteral administration or intravascular injection.

12. The method of claim 11 wherein said sugar composition is administered to said patient by intranasal or intraotic spray or drops, ophthalmic drops or ointment, throat spray, lozenge, liquid gargle, chewable tablet, chewing gum, skin patch, ointment, lotion, or cream, inhaler, or rectal or vaginal suppository.

13. The method of claim 11 wherein the sugar is a monosaccharide, disaccharide, dextran, sugar alcohol, or an amino sugar.

14. The method of claim 13 wherein said sugar is selected from the group consisting of galactose, xylose, fructose, glucose, arabinose, ribose, lyxose, meso-erythritol, xylitol, dulcitol, myo-inositol, mannitol, sorbitol, adonitol, arabitol, cellobiose, maltose, raffinose, rhamnose, melibiose, fucose, maltodextrins, glucosamine, mannosamine, galactosamine, lactose, and sucrose.

15. The method of claim 11 wherein the sugar composition comprises an amino acid or small peptide.

16. The method of claim 15 wherein the amino acid or peptide source is a food enzyme.

17. The method of claim 15 wherein the amino acid is selected from the group consisting of glutamine, lysine, arginine, alanine, isoleucine, asparagine, aspartic acid, cysteine, glutamic acid, glycine, histidine, leucine, methionine, phenylalanine, proline, serine, threonine, tryptophan, tyrosine, valine, taurine, ornithine, carnitine, and citrulline.

18. A method for increasing the passage of a chemical compound through the blood-brain barrier comprising administering said chemical compound to a patient in need thereof, co-administering with said chemical compound a hypertonic sugar composition by a route other than by intravascular injection or enteric administration, and permitting said hypertonic sugar composition to increase the passage of said chemical compound through the blood-brain barrier.

19. The method of claim 18 wherein said administration of said chemical compound is substantially simultaneous with said administration of said hypertonic sugar composition.

20. The method of claim 18 wherein said administration of said chemical compound is before said administration of said hypertonic sugar composition.

21. The method of claim 18 wherein said administration of said chemical compound is after said administration of said hypertonic sugar composition.

22. The method of claim 18 wherein the absorption of said hypertonic sugar composition into the body of said patient is through the nasal, ocular, oral, rectal, vaginal, or upper respiratory mucosa, or through the skin or lungs.

23. The method of claim 18 wherein said sugar is a monosaccharide, disaccharide, dextran, sugar alcohol, or an amino sugar.

24. The method of claim 23 wherein said sugar is selected from the group consisting of galactose, xylose, fructose, glucose, arabinose, ribose, lyxose, meso-erythritol, xylitol, dulcitol, myo-inositol, mannitol, sorbitol, adonitol, arabitol, cellobiose, maltose, raffinose, rhamnose, melibiose, fucose, maltodextrins, glucosamine, mannosamine, galactosamine, lactose, and sucrose.

25. The method of claim 18 wherein said sugar composition comprises an amino acid or a small peptide.

26. The method of claim 25 wherein the amino acid or peptide source is a food enzyme.

27. The method of claim 25 wherein said amino acid is selected from the group consisting of glutamine, lysine, arginine, alanine, isoleucine, asparagine, aspartic acid, cysteine, glutamic acid, glycine, histidine, leucine, methionine, phenylalanine, proline, serine, threonine, tryptophan, tyrosine, valine, taurine, ornithine, carnitine, and citrulline.

* * * * *